US00RE37343B1

(19) United States
(12) Reissued Patent
Tekamp-Olson

(10) Patent Number: US RE37,343 E
(45) Date of Reissued Patent: Aug. 28, 2001

(54) EXPRESSION AND SECRETION OF HETEROLOGOUS PROTEINS IN YEAST EMPLOYING TRUNCATED ALPHA-FACTOR LEADER SEQUENCES

(75) Inventor: Patricia Tekamp-Olson, San Anselmo, CA (US)

(73) Assignee: Chiron Corporation, Emeryville, CA (US)

(21) Appl. No.: 09/140,858

(22) Filed: Aug. 27, 1998

Related U.S. Patent Documents

Reissue of:
(64) Patent No.: 5,602,034
Issued: Feb. 11, 1997
Appl. No.: 08/313,540
Filed: Sep. 27, 1994

U.S. Applications:

(63) Continuation of application No. 07/864,206, filed on Apr. 3, 1992, now abandoned, which is a continuation of application No. 07/670,352, filed on Mar. 13, 1991, now abandoned, which is a continuation of application No. 07/530,477, filed on May 29, 1990, now abandoned, which is a continuation of application No. 07/139,682, filed on Dec. 30, 1987, now abandoned.

(51) Int. Cl.[7] ..... C12N 15/62; C12N 15/09; C12N 1/15; C12N 15/63; C12N 15/81

(52) U.S. Cl. ..... 435/69.9; 435/69.7; 435/69.8; 435/254.2; 435/254.11; 435/320.1; 435/471; 435/483; 536/24.1; 536/24.2; 536/23.4

(58) Field of Search ..... 435/69.9, 254.2, 435/254.11, 320.1, 69.7, 69.8, 471, 483; 536/23.4, 24.1, 24.2

(56) References Cited

U.S. PATENT DOCUMENTS 4,546,082 10/1985 Kurjan et al. ..... 435/172.3
4,870,008 9/1989 Brake ..... 435/70
5,302,697 4/1994 Goodey et al. ..... 530/325

FOREIGN PATENT DOCUMENTS

088632 * 9/1983 (EP) .
0 123 228 10/1984 (EP) .
0 123 294 10/1984 (EP) .
0 171 000 12/1986 (EP) .
0 206 783 12/1986 (EP) .
0 214 826 3/1987 (EP) .

OTHER PUBLICATIONS

Barr, P.J. et al. (eds.), *Yeast Genetic Engineering*, 1989, 239 and 272.

Brake et al., *Mol. Cell. Biol.*, 1983, 3(8), 1440–1450.

Fuller et al., *Microbiology*, 1986, 273–278.

Hitzeman et al., *Science*, 1983, 219, 620–625.

Julius et al., *Cell*, 1983, 32, 839–852.

Rothblatt et al., *EMBO J.*, 1987, 6(11), 3455–3463.

Singh et al., "*Saccharomyces cerevisiae* contains two discrete genes coding for the α–factor pheromone," *Nucl. Acids Res.*, 1983, 11(12), 4049–4063.

Sidhu et al., *Gene*, 1987, 54, 175–184.

Zsebo, K.M. et al., *J. Biol. Chem.*, 1986, 261(13), 5858–5865.

* cited by examiner

*Primary Examiner*—Rebecca E. Prouty
(74) *Attorney, Agent, or Firm*—Francis A. Paintin; Joseph H. Guth; Robert P. Blackburn

(57) ABSTRACT

A yeast α-factor expression system is provided comprised of a truncated leader sequence, containing the α-factor signal peptide and one glycosylation site, linked by a processing site to a non-yeast protein-encoding sequence.

75 Claims, 8 Drawing Sheets

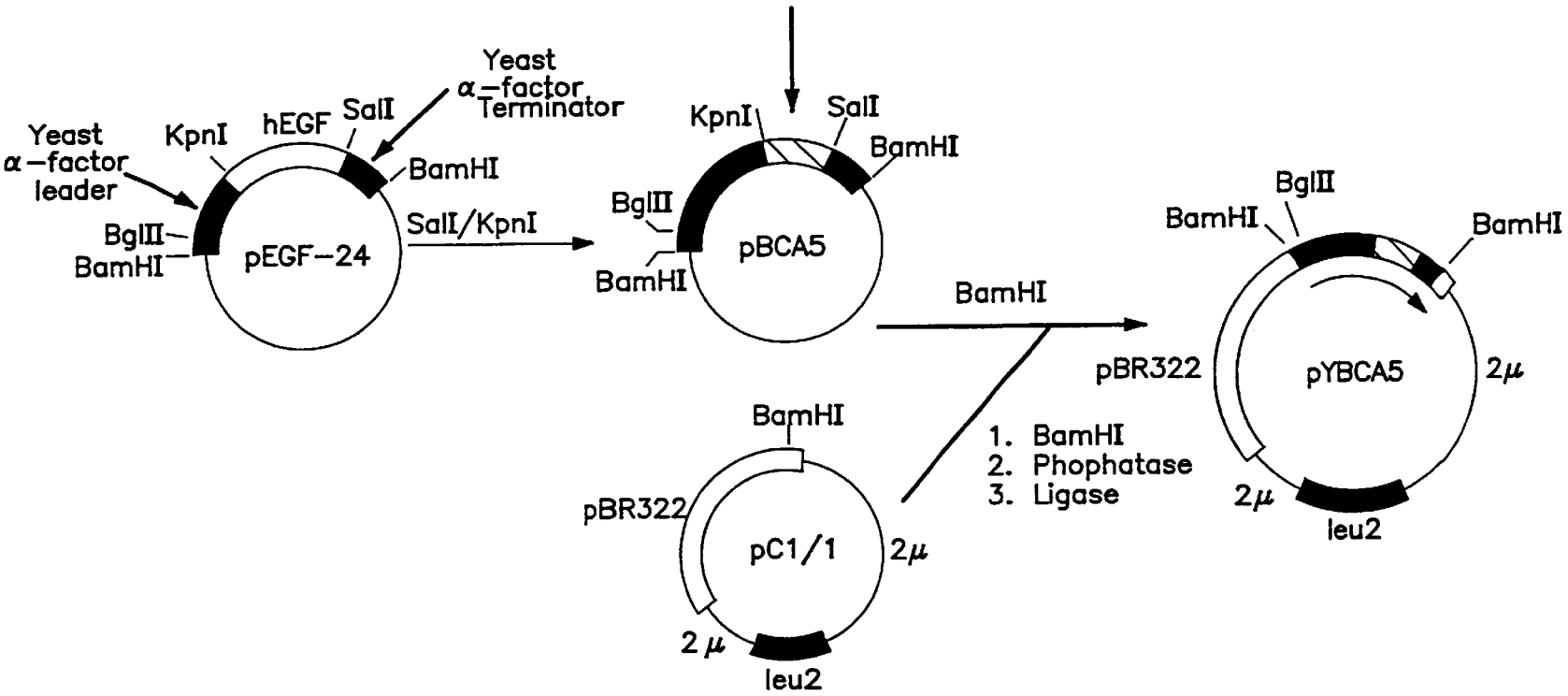
FIG. IB

Sequence of synthetic gene fragment of pYGAI3

```
NLA111   ALU1   HPA11  TAQ1          BBV-1  HINCI1-1
   PST1  BBV-1    ALU1               FNU4H1      HIND111
      BBV-2  MBO11-1                  MBO11-1    ALU1
      FNU4H1       MAE3                 XBA1      RSA1
      SFAN1-1       DDE1                MAE1
      FOK1-2                              HINF1
       MNL1-1                              HPA1
         FNU4H1
         GSU1-1

MetArgPheProSerIlePheThrAlaValLeuPheAlaAlaSerSerAlaLeuAlaAla
CATGAGATTTCCTTCAATTTTTACTGCAGTTTTATTCGCAGCATCCTCCGCATTAGCTGCT
TACTCTAAAGGAAGTTAAAAATGACGTCAAAATAAGCGTCGTAGGAGGCGTAATCGACGA

1 NLA111, 24 PST1, 38 BBV FNU4H1, 41 SFAN1, 42 FOK1, 45 MNL1
, 55 ALU1, 56 BBV FNU4H1, 60 GSU1,

ProValGlnThrThrThrGluAspGluThrAlaGlnIleProAlaGluAlaValIleGly
62 CCAGTCCAAACTACAACAGAAGATGAAACGGCACAAATTCCGGCTGAAGCTGTCATCGGT
GGTCAGGTTTGATGTTGTCTTCTACTTTGCCGTGTTTAAGGCCGACTTCGACAGTAGCCA

80 MBO11, 101 HPA11, 109 ALU1, 120 MAE3,

TyrLeuAspLeuGluGlyAspPheAspValAlaValLeuProPheSerGlnSerThrAsn
122 TACTTAGATTTAGAAGGGGATTTCGATGTTGCTGTTTTGCCATTTTCCCAAAGCACAAAT
ATGAATCTAAATCTTCCCCTAAAGCTACAACGACAAAACGGTAAAAGGGTTTTCGTGTTTA

124 DDE1, 144 TAQ1,

AsnGlyLeuLeuPheIleGlnThrThrIleAlaSerIleAlaAlaLysGluGluGlyVal
182 AACGGGTTATTGTTTATACAAACTACTATTGCCAGCATTGCTGCTAAAGAAGAAGGGGTA
TTGCCCAATAACAAATATGTTTTGATGATAACGGTCGTAACGACGATTTCTTCTTCCCCAT

221 BBV FNU4H1, 230 MBO11,

SerLeuAspLysArgPheValAsnGlnHisLeuCysGlySerHisLeuValGluAlaLeu
242 TCTCTAGATAAAAGATTCGTTAACCAACACTTGTGTGGTTCTCACTTGGTTGAAGCTTTG
AGAGATCTATTTTCTAAGCAATTGGTTGTGAACACACCAAGAGTGAACCAACTTCGAAAC

244 XBA1, 245 MAE1, 255 HINF1, 260 HINC11 HPA1, 294 HIND111,
295 ALU1, 301 RSA1,

Tyr
302 TACTT
ATGAA
```

FIG. 2

Sequence of the Synthetic Gene Fragment of pYGAIC3

```
| |                          |     |           |
HIND3                        RSA1  RSA1        SAL1
ALU1
  RSA1

     GluAlaLeuTyrLeuValCysGlyGluArgGlyPhePheTyrThrProLysThrLysArg
  1  GAAAGCTTTGTACTTGGTTTGTGGTGAAAGAGGTTTCTTCTACACTCCAAAGACTAAGAGA
     CTTCGAAACATGAACCAAACACCACTTTCTCCAAAGAAGATGTGAGGTTTCTGATTCTCT

     2 HIND3, 3 ALU1, 9 RSA1,

     GlyIleValGluGlnCysCysThrSerIleCysSerLeuTyrGlnLeuGluAsnTyrCys
 61  GGTATTGTTGAACAATGTTGTACTTCTATTTGTTCTTTGTACCAATTGGAAAACTACTGT
     CCATAACAACTTGTTACAACATGAAGATAAACAAGAAACATGGTTAACCTTTTGATGACA

     80 RSA1, 99 RSA1,

     AsnOC AM
121  AACTAATAGCGTCGTCGAC
     TTGATTATCGCAGCAGCTG

     134 SAL1,

181
```

FIG. 3

```
                                   TαF_L IGF1
 MET     1.22                                2.45                    ASNTHRTHRSER
CATGAGATTTCCTTCAATTTTTACAGCAGTTTTATTCGCAGCATCCTCCGCATTAGCTGCTCCAGTCAACACTACATCT
    TCTAAAGGAAGTTAAAAATGTCGTCAAAATAAGCGTCGTAGGAGGCGTAATCGACGAGGTCAGTTGTGATGTAGA
                         8.43                                    9.47
                         I2
             3.47                                    4.49
LEUASPLYSARG
CTAGATAAAAGAGGTCCAGAAACCTTGTGTGGTGCTGAATTGGTCGATGCTTTGCAATTCGTTTGTGGTGACAGAGGTT
GATCTATTTTCTCCAGGTCTTTGGAACACACCACGACTTAACCAGCTACGAAACGTTAAGCAAACACCACTGTCTCCAA
                                   10.49
                                                                        6.47
                5.50                                                    I2

TCTACTTCAACAAGCCAACCGGTTACGGTTCTTCTTCTAGAAGAGCCCCACAAACCGGTATCGTTGACGAATGTTGTTT
AGATGAAGTTGTTCGGTTGGCCAATGCCAAGAAGAAGATCTTCTCGGGGTGTTTGGCCATAGCAACTGCTTACAACAAA
         11.48                                           12.51

                                   7.48

                                   I2

CAGATCTTGTGACTTGAGAAGATTGGAAATGTACTGTGCTCCATTGAAGCCAGCTAAGTCTGCTTGATAAG
GTCTAGAACACTGAACTCTTCTAACCTTTACATGACACGAGGTAACTTCGGTCGATTCAGACGAACTATTCAGCT
                         13.48                                   14.22
```

FIG. 5

IGF Plasmid (pYLUIGF 1–24)

EXPRESSION AND SECRETION OF HETEROLOGOUS PROTEINS IN YEAST EMPLOYING TRUNCATED ALPHA-FACTOR LEADER SEQUENCES

Matter enclosed in heavy brackets [ ] appears in the original patent but forms no part of this reissue specification; matter printed in italics indicates the additions made by reissue.

This application is a continuation of application Ser. No. 07/864,206, filed 3 Apr. 1992, now abandoned, which is a continuation of application Ser. No. 07/670,352, filed 13 Mar. 1991, now abandoned, which is a continuation of application Ser. No. 07/530,477, filed 29 May 1990, now abandoned, which is a continuation of application Ser. No. 07/139,682, filed 30 Dec. 1987, now abandoned.

Related U.S. Application Data

This is a reissue of U.S. Pat. No. 5,602,034, Issued, Feb. 11, 1997, incorporated herein by reference in its entirety.

TECHNICAL FIELD

The present invention relates to the production of recombinant proteins in yeast. More particularly, the present invention is directed to an improved α-factor expression system which provides for the secretion of heterologous proteins from yeast host cells.

BACKGROUND

Kurjan et al. (1982) Cell 30:933–943 discloses the first cloning and sequencing of a gene encoding a yeast α-factor precursor gene. Kurjan et al., U.S. Pat. No. 4,546,082, also reports the cloning of this gene, and suggests that the α-factor leader sequence can be employed to direct the secretion of heterologous proteins in yeast. The patent, however, does not contain data which would indicate that the patentees ever successfully employed the α-factor leader to express and secrete a heterologous protein in yeast.

EPO Publication No. 116,201 discloses the first successful application of the α-factor leader to direct the expression and secretion of an heterologous protein, epidermal growth factor, from a transformed yeast. Subsequent to this work, there have been additional reports of the expression of heterologous proteins in yeast employing the α-factor leader. See, e.g., Elliott et al. (1983) Proc. Nat'l Acad. Sci. USA 80:7080–7084; Bitter et al. (1984) Proc. Nat'l Acad. Sci. USA 81:5330–5334; Smith et al. (1985) Science 229:1219–1229; EPO Publication Nos. 114,695; 123,228; 123,294; 123,544; 128,773; and 206,783. See also Brake et al. in *Protein Transport and Secretion,* p. 103 (J. M. Gething ed. 1984).

The expression systems in the above reports produce a full-length α-factor leader fused to a heterologous protein. While the above work demonstrates that the α-factor expression system is widely useful, it is not generally predictable prior to performing the experiment whether a particular heterologous protein will be successfully secreted, processed and biologically active. See, e.g., EPO 206,783, supra, pp. 2–5; Rothblatt et al. (1987) EMBO J. 6:3455–3463; V. L. MacKay, "Secretion of Heterologous Proteins in Yeast" (in press).

There have been several reports, based on unpublished data, that deletions from the "pro" region of the α-factor leader (between the signal peptide and the first spacer) causes substantial declines in the amount of non-yeast protein secreted by yeast transformed the heterologous constructs. Sidhu et al. (1987) Gene 54:175–184, reports that yeast acid phosphatase (PHO5) is secreted into the medium from a heterologous construct employing both a full-length α-factor leader, and a truncated α-factor leader, but that expression levels are 3–4× less than for the PHO5 gene under the control of its homologous leader. It has also been reported that deletions in the prepro-α-factor precursor gene results in substantial declines in secretion of the native α-factor peptide. See, e.g., V. L. MacKay, supra; Rothblatt et al., supra.

A need exists, therefore, to improve the α-factor expression system, particularly for applications to non-yeast proteins that are not efficiently produced by current α-factor expression constructs.

SUMMARY OF THE INVENTION

It has been surprisingly discovered that a truncated form of the α-factor leader sequence can efficiently direct the expression and secretion of heterologous polypeptides in yeast. Particularly surprising is the discovery that truncated α-factor leader sequences can substantially improve the efficiency of expression of such heterologous proteins in relation to expression systems using the full-length α-factor leader; i.e., higher levels of correct N-terminal processing, secretion of heterologous proteins wherein a greater percentage of the molecules are biologically active, etc. These results are particularly surprising in view of reports that deletions from the leader sequence of the α-factor precursor result in decreased levels of secretion of active α-factor.

The present invention provides, therefore, for alternative α-factor-based expression constructs, which are particularly useful for the expression of heterologous polypeptides which are either inefficiently expressed by full-length α-factor leader constructs, or are not expressed at all by such full-length constructs.

In one embodiment, the present invention is directed to a yeast cell comprising a DNA construct that provides for the expression and secretion of a non-yeast protein, said DNA construct comprising a coding sequence under the control of yeast-recognized transcription initiation and termination sequences, said coding sequence encoding a precursor polypeptide comprised of a leader sequence and said non-yeast protein linked by a processing site that provides for the cleavage of said non-yeast protein from said precursor polypeptide, wherein said leader sequence is about 25 to about 50 N-terminal residues of said precursor polypeptide and comprises the signal peptide of a yeast α-factor precursor and a single glycosylation site.

In another embodiment, the present invention is directed to a double-stranded DNA molecule comprising a region encoding a precursor polypeptide secretable by a yeast host, said region, with reference to one of the DNA strands, having the structure:

$$5'\text{-AF-CHO-X}_n\text{-S-Gene*-3'}$$

wherein

AF encodes a yeast α-factor signal peptide; CHO encodes a glycosylation site;

$X_n$ encodes a polypeptide of n amino acids in length that does not contain a glycosylation site or a processing site that provides for cleavage of said precursor polypeptide in vivo by yeast;

n is an integer from 0 to about 30;

Gene* encodes a non-yeast protein; and

S encodes a processing site that provides for cleavage of said precursor polypeptide.

The present invention is also directed to methods of employing the above cells and DNA constructs to produce recombinant proteins, as well as the compositions of recombinant proteins produced by the above methods. Other embodiments will also be readily apparent to those of ordinary skill in the art.

DESCRIPTION OF THE FIGURES

FIG. 2 is the nucleotide and amino acid sequence of a synthetic oligonucleotide encoding a modified α-factor leader and the first 13 amino acids of the proinsulin gene used to construct pYGAI3 in Example I. The modified α-factor leader has had the glycosylation sites removed by changing the codons for $Asn_{23,57,67}$ to encode Gln (boxed). The arrow denotes the junction between the sequence encoding the KEX2 endopeptidase site and the N-terminus of human proinsulin.

FIG. 3 shows the synthetic gene of fragment of pYGAIC3 encoding the proinsulin analog, where a KEX2 endopeptidase site has replaced the C peptide (boxed). The synthetic 133 bp fragment referred to in Example II is defined by the vertical and horizontal lines thru the nucleotide sequence.

FIG. 5 shows the DNA sequence of the synthetic gene encoding IGF1 described in Example III.

DETAILED DESCRIPTION

Figure 1A:
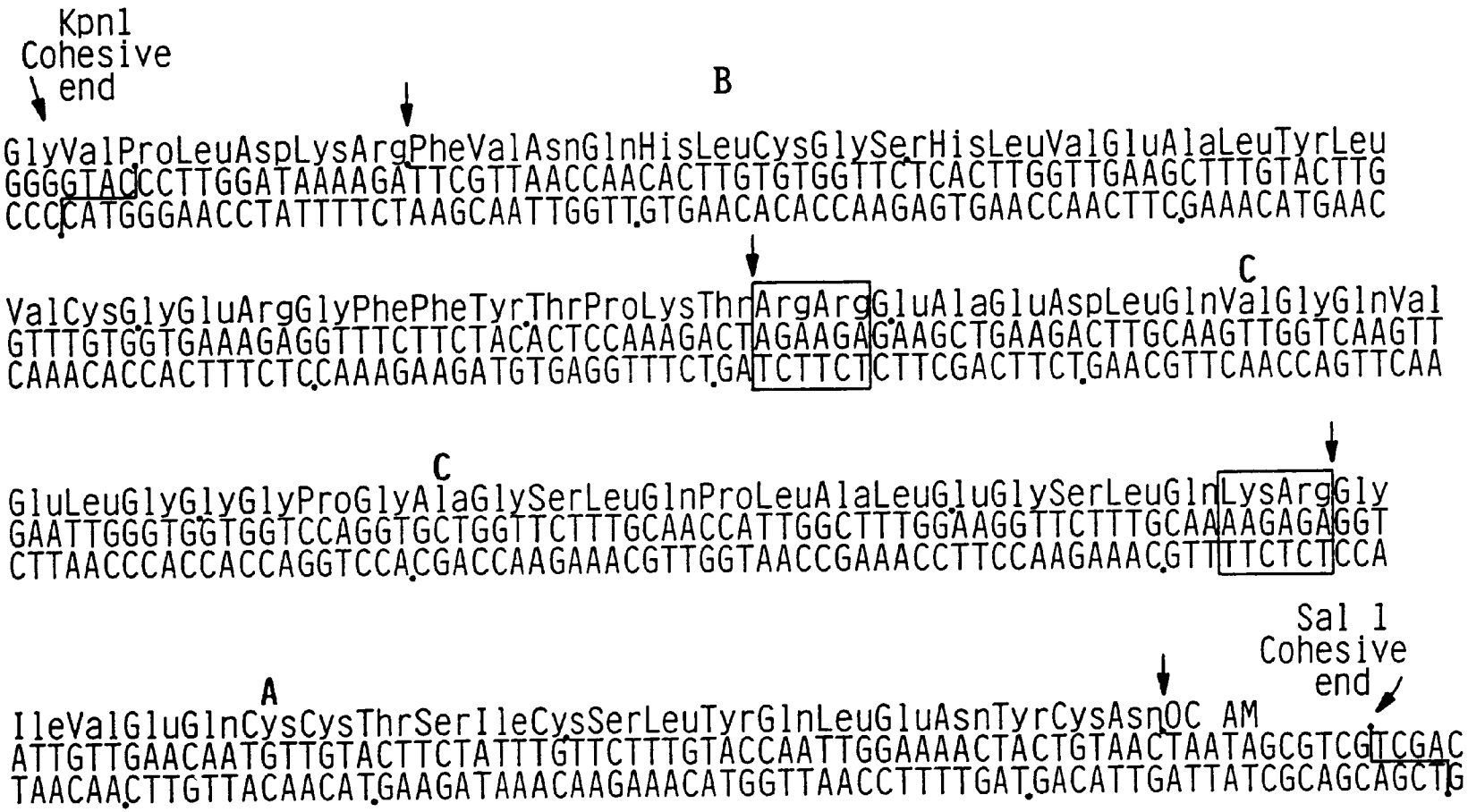
FIG. 1 is a flow diagram showing the construction of pYBCA5, and both the nucleotide and amino acid sequences of the synthetic proinsulin gene employed in Example I. The various synthetic oligonucleotides used in construct are delineated by black dots. Arrows above the sequence show the beginning and end of the B, C and A proinsulin chains. The boxes mark the dibasic processing sites.

The practice of the present invention will employ, unless otherwise indicated, conventional molecular biology, microbiology, and recombinant DNA techniques within the skill of the art. Such techniques are fully explained in the literature. See, e.g., Maniatis, Fritsch & Sambrook, *Molecular Cloning: A Laboratory Manual* (1982); *DNA Cloning,* Vols. I & II (D. N. Glover, ed. 1985); *Oligonucleotide Synthesis* (M. J. Gait, ed. 1984); *Transcription and Translation* (B. D. Hames & S. J. Higgins, eds. 1984); *Immobilized Cells and Enzymes* (IRL Press, 1986); B. Perbal, *A Practical Guide to Molecular Cloning* (1984).

In describing the present invention, the following terminology will be used in accordance with the definitions set out below.

A "replicon" is any genetic element (e.g., plasmid, cosmid, chromosome, virus) that functions as an autonomous unit of DNA replication in vivo—i.e., capable of replication under its own control.

A "vector" is a replicon such as a plasmid, phage, or cosmid to which another DNA segment may be attached so as to bring about the replication of the attached segment.

A "double-stranded DNA molecule" refers to the polymeric form of deoxyribonucleotides (adenine, guanine, thymidine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of a particular double-stranded DNA molecule, sequences will be described herein according to the normal convention of giving only the sequence in the 5' to 3' direction along the nontranscribed strand of DNA, i.e., the strand having a sequence homologous to the mRNA produced from a particular coding sequence.

A DNA "coding sequence" is DNA sequence which can be transcribed and translated into a polypeptide in vivo when placed under the control of appropriate regulatory sequences. The boundaries of the coding sequence are determined by and include the translation start codon at the 5' (amino) terminus, and a translation stop codon at the 3' (carboxy) terminus. A coding sequence can include, but is not limited to, procaryotic DNA sequences, vital DNA sequences, cDNA or genomic DNA sequences from eucaryotic sources (e.g., mammalian), and even synthetic DNA sequences.

"Yeast-recognized transcription initiation and termination sequences" refer to DNA regulatory regions which flank a coding sequence and are responsible for the transcription in yeast of an mRNA homologous to the coding sequence which can then be translated into the polypeptide encoded by the coding sequence. Transcription initiation sequences include yeast promoter sequences, which are DNA regulatory sequences capable of binding yeast RNA polymerase in a cell and initiating transcription of a downstream (3' direction) coding sequence. For the purposes of defining the present invention, the promoter sequence is bounded (and excludes) at its 3' terminus by the translation start codon of a coding sequence and extends upstream (5' direction) to include the minimum number of nucleotides or elements necessary to initiate transcription at levels detectable above background. Within the promoter sequence will be found a transcription initiation site (conveniently defined by mapping with nuclease S1), as well as protein-binding domains (consensus sequences) responsible for the binding of the yeast RNA polymerase. Promoters useful in the present invention include the wild-type α-factor promoter, as well as other yeast promoters. Particularly preferred are promoters involved with the enzymes in the glycolytic pathway, e.g., phosphoglucoisomerase, phosphofructokinase, phosphotrioseisomerase, phosphoglucomutase, enolase, pyruvic kinase, glyceraldehyde-3-phosphate dehydrogenase, alcohol dehydrogenase, as well as hybrids of these promoters. See, e.g., EPO Publication Nos. 120, 551; 164,556. Transcription initiation sequences can also include other regulatory regions responsible for promoter regulation or enhancement. In like manner, a transcription terminator sequence located 3' to the translation stop codon can be either the wild-type α-factor transcription termination sequence, or another yeast-recognized termination sequence, such as those from the genes for the above glycolytic enzymes.

A coding sequence is "under the control" of transcription initiation and termination sequences when RNA polymerase binds the transcription initiation sequence and transcribes the coding sequence into mRNA terminating at the transcription termination sequence, and the mRNA is then translated into the polypeptide encoded by the coding sequence (i.e., "expression"). The precursor polypeptide encoded by the coding sequences of the present invention is "secreted" when at least a portion (usually the non-yeast protein in the absence of the leader sequence) is transported extracellularly where it is found in the cell growth medium. Usually, only the portion of precursor protein downstream from the lead sequence is secreted, and this downstream portion may also be subjected to additional processing during secretion, such as proteolytic cleavage, glycosylation, folding, disulfide bond formation, etc.

A cell has been "transformed" by exogenous DNA when such exogenous DNA has been introduced inside the cell wall. Exogenous DNA may or may not be integrated (covalently linked) to chromosomal DNA making up the genome of the cell. The exogenous DNA may be maintained extrachromosomally on a replicon such as a plasmid. When the exogenous DNA has become integrated to the chromosome, it is inherited by daughter cells through chromosome replication. A cell which has been transformed by exogenous DNA which is integrated into the chromosome is referred to as a "stably" transformed cell. A "clone" or "clonal population" is a population of cells derived from a single cell or common ancestor by mitosis.

Two DNA sequences are "substantially homologous" when at least about 60% (preferably at least about 75%, and most preferably at least about 90%) of the nucleotides match over a defined length of the molecules. Sequences that are substantially homologous can be identified in a Southern hybridization experiment under conditions of a selected stringency as defined for that particular system. Defining appropriate hybridization conditions is within the skill of the art. See, e.g., Maniatis et al., supra; *DNA Cloning,* supra; *Nucleic Acid Hybridization,* supra.

A "heterologous region" of a DNA molecule is an identifiable segment of DNA within a larger DNA molecule that is not found in association with the larger molecule in nature. Thus, when the heterologous region encodes a mammalian protein, the heterologous region will usually be flanked by DNA that does not flank the mammalian DNA sequence in the genome of the source organism. Another example of a heterologous coding sequence is a construct where the coding sequence itself is not found in nature (e.g., a cDNA where the genomic coding sequence contains introns, or synthetic sequences having codons different from organisms which encode the same or similar protein). Allelic variations or naturally occurring mutational events do not give rise to a "heterologous" region of DNA as used herein.

As used herein, "yeast" includes ascosporogenous yeasts (Endomycetales), basidiosporogenous yeasts and yeast belonging to the Fungi imperfecti (Blastomycetes). The scosporogenous yeasts are divided into two families, Spermophthoraceae and Saccharomycetaceae. The latter is comprised of four subfamilies, Schizosaccharomycoideae (e.g., genus Schizosaccharomyces), Nadsonioideae, Lipomycoideae and Saccharomycoideae (e.g., genera Pichia, Klyveromyces and Saccharomyces). The basidiosporogenous yeasts include the genera Leucosporidium, Rhodosporidium, Sporidiobolus, Filobasidium and Filobasidiella. Yeast belonging to the Fungi Imperfecti are divided into two families, Sporobolomycetaceae (e.g., genera Sporobolomyces, Bullera) and Cryptococcaceae (e.g., genus Candida). Of particular interest to the present invention are species within the genera Pichia, Kluyveromyces, Saccharomyces, Schizosaccharomyces and Candida. Of particular interest are the Saccharomyces species *S. cerevisiae, S. carlsbergensis, S. diastaticus, S. douglasii, S. kluyveri, S. norbensis* and *S. oviformis.* Species of particular interest in the genus Kluyveromyces include *K. lactis.* Since the classification of yeast may change in the future, for the purposes of this invention, yeast shall be defined as described in *Biology and Activities of Yeast* (F. A. Skinner, S. M. Passmore & R. R. Davenport eds. 1980) (Soc. App. Bacteriol. Symp. Series No. 9). In addition to the foregoing, those of ordinary skill in the art are presumably familiar with the biology of yeast and the manipulation of yeast genetics. See, e.g., *Biochemistry and Genetics of Yeast* (M. Bacila, B. L. Horecker & A. O. M. Stoppani eds. 1978); *The Yeasts* (A. H. Rose & J. S. Harrison eds., 2nd ed., 1987); *The Molecular Biology of the Yeast Saccharomyces* (Strathern et al. eds. 1981). The disclosures of the foregoing references are incorporated herein by reference.

The present invention employs truncated leader sequences from a yeast α-factor gene. α-factor is an oligopeptide mating pheromone about 13 residues in length produced from a large precursor polypeptide between about 100 and 200 residues (typically about 120–160) in length (prepro-α-factor). The precursor is comprised of a hydrophobic "signal sequence" of about 20 residues (e.g., about 19–23, typically about 20–22) followed by an additional leader region of about 60 hydrophilic residues (the "pro" region), which is then linked to several tandem repeats of the mature pheromone sequence (typically about 2–6) separated by short oligopeptide spacer regions (typically about 6–8 residues) which provide for proteolytic processing to the mature pheromone.

The cloning of various prepro-α-factor genes has been reported. See, e.g., Kurjan et al., U.S. Pat. No. 4,546,082; Singh et al. (1983) Nucleic Acids Res. 11:4049–4063; commonly owned U.S. patent application Ser. No. 078,551, filed 28 Jul. 1987, now U.S. Pat. No. 5,010,182, the disclosure of which is incorporated herein by reference. In addition, DNA sequences encoding the prepro-α-factor gene can be identified by hybridization with probes from known prepro-α-factor sequences. See, e.g., Brake et al. (1983) Molec. & Cell Biol. 3:1440–1450. α-factor may also be purified from a yeast species, sequenced and probes designed to clone the prepro-α-factor gene. See, e.g., McCullough et al. (1979) J. Bacteriol. 138:146–154; Sato et al. (1981) Agric. Biol. Chem. 44:1451–1453; Singh et al. (1983), supra. It has also been determined that the α-factor leader sequence from one yeast species can be functional in another yeast species. See, e.g., U.S. Ser. No. 078,551, supra. Thus, the present invention contemplates not only the use of α-factor leader sequences from yeast in general, but the use of such leader sequences in heterologous yeast species. For ease of presentation, however, the invention will be discussed in terms of the prepro-α-factor gene MFα1 from *S. cerevisiae.* See, e.g., Kurjan et al., U.S. Pat. No. 4,546,083; Singh et al. (1983), supra.

The present invention employs chimetic DNA constructs encoding hybrid precursor polypeptides comprised of a leader sequence and a non-yeast polypeptide. For purposes Of this invention, the leader sequence DNA is defined as beginning at the N-terminal start codon (methionine) of the precursor polypeptide through the codon encoding the last amino acid residue before the processing site that intervenes between the leader sequence and the sequence encoding the non-yeast protein. The leader sequence of the present invention is comprised of a truncated form of a yeast α-factor leader sequence, typically about 25 to about 50 amino acid residues in length. Thus, the leader sequence of the present invention is approximately 30 amino acid residues shorter than the typical full-length α-factor leader. MFα1, for example, contains a leader sequence of 83 amino acid residues followed by a hexapeptide spacer sequence which is cleaved by yeast processing enzymes. In making deletions from the leader sequence, it is important that at least one glycosylation site (-Asn-Y-Thr/Ser-) is retained to provide for efficient secretion.

It is also necessary that the leader retain a functional α-factor signal sequence. As indicated above, the signal peptide is usually about 20 amino acids in length, and characteristic features including a hydrophobic core. See, e.g., von Heijne, (1984) J. Mol. Biol. 173:243–251. All of the prepro-α-factor sequences examined today encode for a hydrophobic peptide of about 20 residues in length. While the exact length of a signal peptide necessary to direct the precursor polypeptide to the secretory pathway is not defined, it will usually require between about 19 and about 23 residues, the minimum sequence required being readily definable by the testing of deletion mutants.

Thus, with reference to MFα1, deletions within the range of about 30 to about 60 residues, typically between about 33 and about 58 residues, and more typically between about 48 and about 58 residues, is contemplated by the present invention. These deletions will generally occur in the region between and including residues 26 through 83. It is preferred that the deletions include the glycosylation sites at residues 57–59 and 67–69. The deleted α-factor leader sequences may be replaced, in part, by non-α-factor leader sequences, if desired. The sequences should generally encode hydrophilic amino acid residues, should not encode glycosylation or processing sites, and preferably should be selected to maintain the overall length of the leader to be about 50 residues or less, preferably about 23 to 40 residues, and most preferably about 25 to 35 residues.

As indicated above, the leader sequence of the present invention has immediately 3' thereto a processing site which allows for the cleavage of the leader from the non-yeast protein sequence to which it is fused in the precursor polypeptide. The processing site employed in the present invention is defined as the codons defining the minimum number of amino acid residues which are specifically recognized for cleavage by the selected process (e.g., chemical, enzymatic, etc.). Various processing sites are known in the art, including both those active in vivo and in vitro. For example, the processing site may provide for in vitro processing by encoding a cleavage site for a proteolytic enzyme which does not occur in the yeast host. The recovered precursor polypeptide would then be treated with the enzyme to cleave the non-yeast protein from the precursor. Another in vitro processing site is a methionine codon which can be cleaved by post-expression treatment with cyanogen bromide. See, e.g., U.S. Pat. No. 4,366,246.

In vivo processing sites can be selected from any peptide signals recognized by a yeast proteolytic enzyme which will provide for expression of the desired non-yeast protein sequence. Particularly preferred processing sites are those for the enzymes involved in processing of native prepro-α-factor. For example, dipeptidyl aminopeptidase A (DPAPase A) removes terminal -X-Ala- sequences, where X is Glu or Asp. See, e.g., Julius et al. (1983) Cell 32:839–852. The endopeptidase encoded by the KEX2 gene cleaves basic dipeptides comprised of Lys and Arg residues; i.e., Lys-Arg, Arg-Arg, Arg-Lys and Lys-Lys. Fuller et al., *Microbiology* 1986, pp. 273–278 (1986). In yeast, the α-factor precursor is first cleaved by the KEX2 endopeptidase, and then the N-termini are trimmed by DPAPase A to provide mature α-factor pheromone. Since it appears that the latter proteolytic process is a rate limiting step, it is preferred to eliminate the signals for DPAPase A, such that the processing site is comprised only of the signal for the KEX2 endopeptidase. In such an embodiment, therefore, the leader sequence will be joined to the non-yeast protein sequence by the dibasic peptide recognition site for KEX2 endopeptidase, such as Lys-Arg or Arg-Arg.

The carboxy-terminal portion of the precursor polypeptide of the present invention is a non-yeast protein. The DNA sequence encoding this portion is defined herein as beginning with the first codon downstream (3' direction) from the last codon of the processing site through to the translation stop codon which defines the carboxy-terminal of the precursor polypeptide. This DNA sequence will be considered to encode a "non-yeast protein" when, over its entire sequence, it defines a polypeptide that is not substantially homologous to a polypeptide expressed by yeast. In general, the preferred non-yeast proteins will be mammalian protein sequence (including their analogs; i.e., "muteins", fragments, etc) As defined herein, non-yeast proteins can include, therefore, a fusion protein comprised of mammalian and yeast sequences, as well as "pro" forms of the mature mammalian protein.

DNA sequences encoding the non-yeast proteins can be sequences cloned from non-yeast organisms, or they can be synthetic sequences, usually prepared using yeast-preferred codons. Usually, the non-yeast proteins will be at least about 8 amino acids in length and can include polypeptides up to about 100,000 daltons or higher. Usually, the non-yeast polypeptide sequence will be less than about 300,000 daltons, and more usually less than about 150,000 daltons. Of particular interest are polypeptides of from about 5,000 to about 150,000 daltons, more particularly of about 5,000 to about 100,000 daltons. Illustrative non-yeast proteins of interest include hormones and factors, such as growth hormone, somatomedins, epidermal growth factor, luteinizing hormone, thyroid-stimulating hormone, oxytocin, insulin, vasopressin, renin, calcitonin, follicle-stimulating hormone, prolactin, erythropoietin, colony-stimulating factors, lymphokines such as interleukin-2, globins, immunoglobulins, interferons (e.g., α, β or γ), enzymes, β-endorphin enkephalin, dynorphin, insulin-like growth factors, etc.

In a preferred embodiment of the present invention, DNA constructs encoding the above-described precursor polypeptides have the structure:

5'-AF-CHO-$X_n$-S-Gene*-3' wherein AF encodes a yeast alpha-factor signal peptide; CHO encodes a glycosylation site; $X_n$ encodes a polypeptide of n amino acids in length that does not contain a glycosylation site or processing site that will cause the precursor polypeptide to be cleaved in vivo by the yeast host; n is an integer from 0 to about 30; Gene* encodes a non-yeast protein; and S encodes a processing site that provides for cleavage of said precursor polypeptide.

The signal peptide encoded by AF is the same α-factor signal peptide described above. It is approximately 20 residues in length (e.g., about 19–23) and is of sufficient length to direct the precursor polypeptide into the yeast secretory pathway. The precise minimum or maximum length can be determined for a particular α-factor by screening a series of deletion constructs.

The DNA sequence defined by CHO encodes a glycosylation site. It will generally be nine nucleotides in length, including three codons for the amino acids Asn-Y-Y'-, wherein Y is any amino acid residue, and Y' is Thr or [Set] *Ser*.

$X_n$, if present, encodes, for example, portions of the α-factor leader which are not deleted or unrelated amino acid sequences. In general, $X_n$ will be a maximum of about 30 amino acid residues, more preferably a maximum of about 20 residues, and most preferably a maximum of about 10 residues. While it may not be necessary for $X_n$ to encode any polypeptides (i.e., n=0), it may be desired to provide some spacing between the glycosylation site CHO, and the processing site S in the event that carbohydrate additions at the glycosylation site sterically hinder access of the agent which cleaves the processing sites. In such case, n will usually be a minimum of about 1, more preferably a minimum of about 2, while most preferably a minimum of about 3.

It is preferred that $X_n$, if present, not contain any functional glycosylation sites or processing sites recognized and cleaved by the yeast host. Further, when departing from sequences found in an α-factor leader, it is preferred to select hydrophilic amino acid residues. It is possible that the length of $X_n$ will affect the efficiency of expression and secretion of the non-yeast protein. Selection of the appropriate length of $X_n$ to optimize expression can be done through screening constructs of various sizes.

The non-yeast protein encoded by Gene* and the processing site encoded by S are as described above.

The DNA constructs of the present invention will normally be maintained in a replicon capable of stable maintenance in a host, particularly a yeast host. The replicons, usually plasmids, will include one or more replication systems, desirably two replication systems, allowing for maintenance of the replicon in both a yeast host for expression, and in a procaryotic host for cloning. Examples of such yeast-bacteria shuttle vectors include YEp24 [Botstein et al. (1979) Gene 8:17–24], pC1/1 [Brake et al. (1984) Proc. Natl. Acad. Sci. USA 81:4642–4646], and YRp17 [Stnichomb et al. (1982) J. Mol. Biol. 158:157]. Furthermore, a plasmid expression vector may be a high or low copy number plasmid, the copy number generally ranging from about 1 to about 200. With high copy number yeast vectors, there will generally be at least 10, preferably at least 20, and usually not exceeding about 150 copies in a single host. Depending upon the non-yeast protein selected, either a high or low copy number vector may be desirable, depending upon the effect of the vector and the foreign protein on the host. See, e.g., Brake et al., supra. DNA constructs of present invention can also be integrated into the yeast genome by an integrating vector. Examples of such vectors are known in the art. See, e.g., Botstein et al., supra.

The selection of suitable yeast and other microorganism hosts for the practice of the present invention is within the skill of the art. When selecting yeasts hosts for expression, suitable hosts may include those shown to have, inter alia, good secretion capacity, low proteolytic activity, and overall robustness. Yeast and other microorganisms are generally available from a variety of sources, including the Yeast Genetic Stock Center, Department of Biophysics and Medical Physics, University of California, Berkeley, Calif.; and the American Type Culture Collection, Rockville, Md.

Methods of introducing exogenous DNA into yeast hosts are well known in the art. There is a wide variety of ways to transform yeast. For example, spheroplast transformation is taught, for example, by Hinnen et al. (1978) Proc. Natl. Acad. Sci. USA 75:1919–1933, and Stinchcomb et al., EPO Publication No. 45,573. Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced. The secreted, processed non-yeast protein can be harvested by any conventional means, and purified by chromatography, electrophoresis, dialysis, solvent-solvent extraction, and the like.

EXAMPLES

The following examples are provided for illustrative purposes only, and are not intended to limit the scope of the present invention. It is believed that the deposit of the starting biological materials is not necessary for the practice of the present invention since either the same or equivalent materials are publicly available.

Example I

The following example provides a comparison of the levels of expression and secretion obtained with modified α-factor constructs used to express human proinsulin. Three constructs employ full-length α-factor leaders; one having α-factor leader with the three native glycosylation sites, one having all three of the glycosylation sites eliminated, and one having all of the sites, except the one at $Asn_{23}$, removed. The fourth construct is a truncated α-factor leader which retains a single glycosylation site at $Asn_{23}$.

A. pYGAI1

This plasmid encodes an α-factor leader [Brake et al. (1984) Proc. Natl. Acad. Sci. USA 81:4642–4646; EPO Publication No. 116,201] linked to human proinsulin. The proinsulin is encoded by a synthetic gene made with yeast preferred codons (FIG. 1). The α-factor leader sequence, the synthetic proinsulin gene and the α-factor terminator sequence are from pYBCA5, the construction of which is shown in FIG. 1. Transcription is mediated by the 404 bp BamHI-NcoI GAPDH promoter fragment. Travis et al. (1985) *J. Biol. Chem.* 260:4384–4389. The 1206 bp BamHI expression cassette consisting of the GAPDH promoter, the sequence encoding the α-factor leader linked to proinsulin and the α-factor terminator was cloned into the unique BamHI site of the yeast shuttle vector pAB24 (below) or pC1/1 such that the GAPDH promoter sequence was proximal to the SalI site of the vector to give the plasmids pYGAI1-AB24 or pYGAI1-C1/1, respectively. The 1206 bp BamHI expression cassette was also subcloned into the unique BamHI site of a derivative of pBR322 [pBR322 (ΔEcoRI-SalI)BamHI; Travis et al. supra.] This plasmid was called pGAI1.

Figure 4:
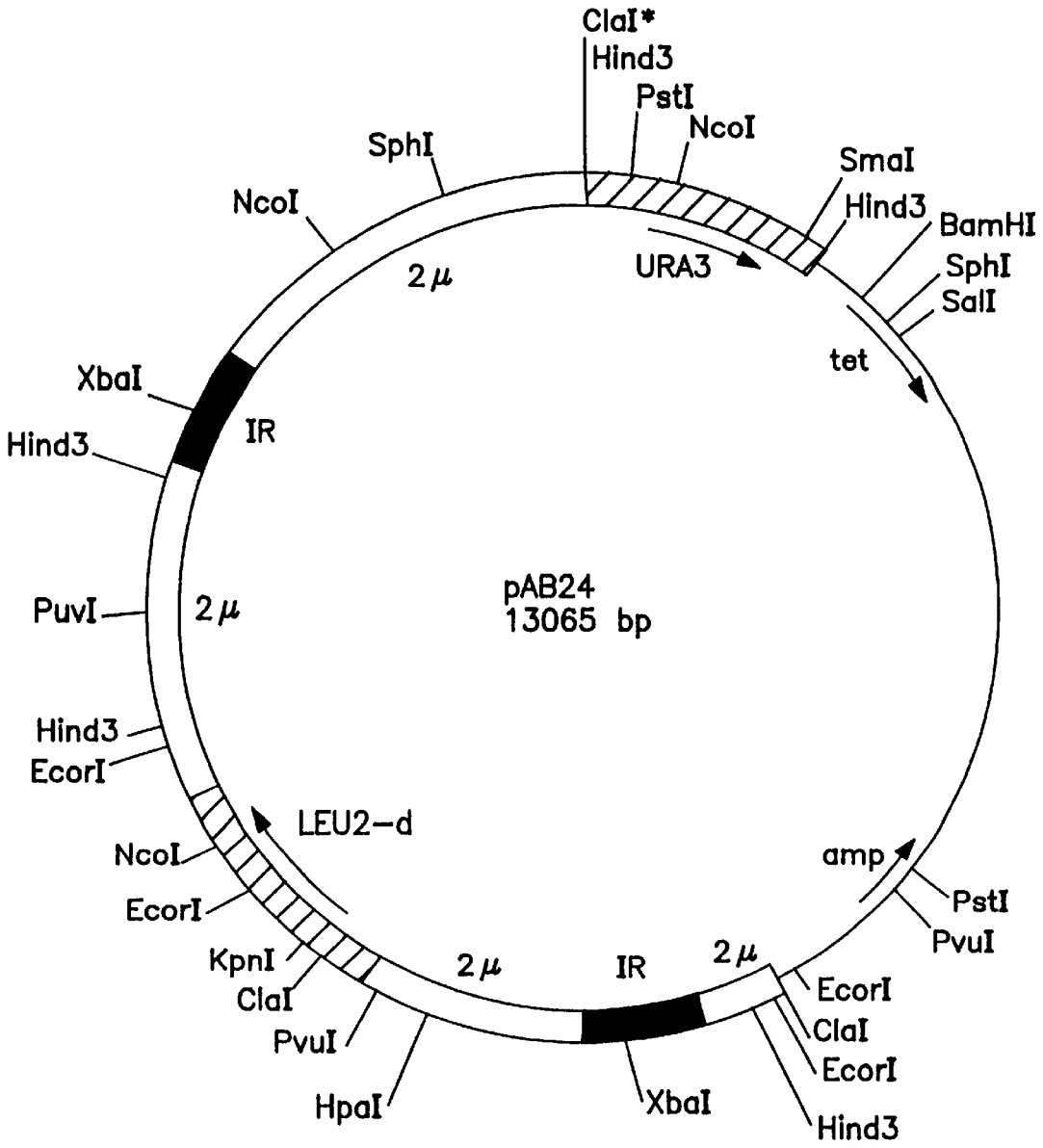
FIG. 4 is a restriction map of yeast shuttle vector pAB24.

Plasmid pAB24 (FIG. 4) is a yeast shuttle vector which contains the complete 2μ sequence [Broach, in: *Molecular Biology of the Yeast Saccharomyces,* Vol., 1, p. 445 (1981)] and pBR322 sequences. It also contains the yeast URA3 gene derived from plasmid YEp24 [Botstein et al. (1979) Gene 8:17] and the yeast LEU2d gene derived from plasmid pC1/1. EPO Publication No. 116,201. Plasmid pAB24 was constructed by digesting YEp24 with EcoRI and religating the vector to remove the partial 2μ sequences. The resulting plasmid, YEp24ΔRI, was linearized by digestion with ClaI and ligated with the complete 2μ plasmid which had been linearized with ClaI. The resulting plasmid, pCBou, was then digested with XbaI and the 8605 bp vector fragment was gel isolated. This isolated XbaI fragment was ligated with a 4460 bp XbaI fragment containing the LEU2d gene isolated from pC1/1; the orientation of the LEU2d gene is in the same direction as the URA3 gene.

B. pYGAI3

Plasmid pYGAI3 differs from pYGAI1 in that it encodes a modified α-factor leader wherein the codons for Asn at residues 23, 57 and 67 have been changed to encode Gln, thereby eliminating all three signals for N-linked glycosylation.

The α-factor leader and the N-terminal 13 amino acids of proinsulin encoded by this plasmid were constructed by ligation of synthetic oligonucleotides to give a 294 bp fragment with a 5' NcoI overhang and a 3' HindIII overhang, the sequence which is shown in FIG. 2. The sequence of appropriate oligonucleotides was altered during the synthesis so that codons which specified Asn at positions 23, 57 and 67 of the natural α-factor leader now specified Gln at the same positions. The DNA sequence specifying the N-terminal 13 amino acids of proinsulin was identical to that in pYGAI1. The 294 bp synthetic DNA (NcoI-HindIII) fragment was substituted for the comparable fragment of pGAI1 and pYGAI1-C1/1 which gave the plasmids pGAI3 and pYGAI3, respectively.

C. pYGAI8

Plasmid pYGAI8 contains DNA encoding an α-factor leader which eliminates two of the three glycosylation sites. $Asn_{57,67}$ have been modified to $Gln_{57,67}$. The resulting plasmid has only a single glycosylation site at position $Asn_{23}$. pYGAI8 was prepared as follows.

First, a 5' fragment was isolated from the expression cassette of pGAI1 by cutting with HpaII, followed by cutting with BamHI, and then gel isolating a 504 bp fragment containing the GAPDH promoter and the sequence encoding residues 1–33 of the α-factor leader. Next, plasmid pYGAI3 encoding an α-factor leader lacking glycosylation sites was also sequentially cut with HpaII and BamHI, and a 702 bp fragment isolated containing sequences encoding modified α-factor leader residues 34–83, the LysArg processing site, the proinsulin sequence and the α-factor termination sequence. This fragment was then ligated to the 504 bp fragment from pGAI1, cut with BamHI and a 1206 bp fragment isolated.

The above 1.2 kb BamHI fragment which contained a complete GAPDH promoter/α-factor leader/proinsulin/α-factor terminator expression cassette was then ligated into BamHI-cut and phosphatase-treated pBR322(AEcoRI-SalI-)BamHI to give plasmid pGAI8, which was cloned in *E. coli.*

The 1.2 kb expression cassette from pGAI8 was removed by cutting with BamHI and then gel isolating the fragment. It was ligated into BamHI-cut and phosphatase-treated yeast shuttle vector pAB24. Insertion of the expression cassette was in the unique BamHI site of the pBR322 sequences such that the GAPDH promoter was proximal to the unique SalI site of the vector. This plasmid was pYGAI8.

D. pYGAI7

Plasmid pYGAI7 contains the DNA encoding a truncated α-factor leader and the synthetic gene for human proinsulin. The α-factor leader has been truncated so that it encodes only amino acids 1–35 of the α-factor leader and therefore contains a single site for glycosylation at $Asn_{23}$. This yeast expression vector was constructed as follows.

First, pGAI1 was cut with HindIII. An HPaII-HindIII linker was added of the following structure:

```
5'-CGGCTAAAAGATTCGTTAACCAACACTTGTGTGGTTCTCACTTGGTTGA
    CGATTTTCTAAGCAATTGGTTGTGAACACACCAAGAGTGAACCAACTTCGA-5'
```

After adding the linker, the linearized plasmid was cut with BamHI, and a 558 bp HpaII-BamHI fragment was gel isolated. This fragment contains the codons for residues 34–35 of the α-factor leader linked directly to a Lys-Arg processing site and the proinsulin sequence. There are no intervening sequences between the codon for residue 35 of the α-factor leader and the processing site directly adjacent to the proinsulin sequence.

Second, pGAI1 was cut with HpaII and BamHI, and a 504 bp fragment gel isolated. This fragment contains the GAPDH promoter and nucleotides encoding amino acids 1–33 of the α-factor leader, the 3' end terminating in an HpaII overhang complementary to the 5' end of the above-described 558 bp HpaII-BamHI fragment. These two fragments were ligated together and cut with BamHI to provide an expression cassette containing the GAPDH promoter, sequences encoding a modified α-factor leader containing residues 1–35 directly linked to a Lys-Arg processing site, the proinsulin gene, and the α-factor terminator. The cassette was then ligated into a BamHI site of pBR322(ΔEcoRI-SalI) BamHI, as described above, to give plasmid pGAI7 and cloned in *E. coli.* pGAI7 was then cut with BamHI, and the 1062 bp expression cassette gel isolated. The expression cassette was then ligated into the BamHI site of pAB24 to give plasmid pYGAI7.

E. Comparative Expression

Plasmids pYGAI1-G1/1, pYGAI3, pYGAI1-AB24, pYGAI7 and pYGAI8 were transformed into *Saccharomyces cerevisiae* strain AB103.1 (Matα, leu2-3,112,ura3-52, his4-580, pep4-3[cir°]) essentially as described by Hinnen et al. (1978) Proc. Natl. Acad. Sci. USA 75:1929–1933. Transformants of pYGAI1-C1/1 and pYGAI3 were selected for leucine prototrophy, transformants of the other plasmids were selected for ura prototrophy.

Data shown in Table 1 compares secretion of proinsulin mediated by the natural α-factor leader (pYGAI1-C1/1) or the α-factor leader with Gln substituted for Asn at positions 23, 57 and 67 (pYGAI3). Inoculum cultures (~2 ml of individual transformants) were grown for 48 hr in synthetic complete medium lacking leucine [SD-leu; Sherman et al., *Methods in Yeast Genesis,* p. 62 (Cold Spring Harbor Laboratory, 1982)] and diluted 20-fold into the same medium. Cultures were grown 48–72 hrs, culture supernatants were prepared by centrifugation and were assayed for immunoreactive cross-reacting insulin-like material (ILM) in a competition radioimmune assay with $^{125}$I-labeled insulin. As can be seen in Table 1, elimination of the three glycosylation sites from the α-factor leader resulted in essentially no secretion of insulin-like-material compared to that mediated by the native α-factor leader.

Data presented in Table 2 compares transformants of pYGAI1-pAB24 (full-length native α-factor leader), pYGAI8 (full-length α-factor leader with only one glycosylation site at $Asn_{23}$) and pYGAI7 (truncated α-factor leader containing a single glycosylation site at $Asn_{23}$) for their ability to secrete insulin-like-material. Inoculum cultures of the indicated transformants (~2 ml) in SD-Leu grown for ~48 hr at 30° C. were pelleted by centrifugation washed and diluted 20–50 fold into ura$^-$ medium. This medium contains 0.67% yeast nitrogen base, 1% succinic acid, 0.35% NaOH, 0.5% casamino acids, 2% glucose, 0.005% adenine, 0.01% tryptophan and 0.02% threonine.

Cultures were grown at 30° C. for 48–72 hr, and culture supernatants prepared and assayed as described above. Data presented in Table 2 show that the transformants carrying the construct employing the truncated α-factor leader retaining a single glycosylation site at $Asn_{23}$ secreted generally more immunoreactive insulin-like-material than did transformants bearing the construct with the full-length native α-factor leader. Transformants bearing the construct with the full-length α-factor leader with the same single glycosylation site ($Asn_{23}$) secreted much less insulin cross-reactive material than did transformants bearing the full-length native α-factor leader or the truncated α-factor leader.

TABLE 1

Effect of Elimination of α-Factcr Leader Glycosylation Sites on Secretion of Insulin-Like-Material

| Transformant | | $OD_{650}$ | ILM[1] μg/ml | ILM[1] μg/ml, $OD_{650}$ |
|---|---|---|---|---|
| AB103.1[pYGAI1-C1/1] | −1 | 5.9 | .24 | .04 |
| | −2 | 5.9 | .24 | .04 |
| | −3 | 2.1 | .08 | .04 |
| AB103.1[pYGAI3] | −1 | ND | .003 | — |
| | −2 | ND | .007 | — |

[1]Cross-reactive insulin-like-material (ILM) as determined by a competition radioimmune assay with $^{125}$I-labeled insulin and insulin standards. Data is reported as ILM secreted per ml of culture and in some cases as ILM secreted per ml normalized to a culture cell density with an absorbance at wavelength 650 mμ of 1.

TABLE 2

Effect of Truncated or Full-Length α-Factor Leader with a Single Glycosylation Site as $Asn_{23}$ on Secretion of Insulin-Like-Material

| Transformant | No. of Tests[1] | ILM[2] μg/ml Range | ILM[2] μg/ml Mean | ILM[2] μg/ml Std. dev. | ILM[2] μg/ml $OD_{650}$ Range | ILM[2] μg/ml $OD_{650}$ Mean | ILM[2] μg/ml $OD_{650}$ Std. dev. |
|---|---|---|---|---|---|---|---|
| AB103.1 [pYGA11-AB24] | 7 | .22–.55 | .37 | .22 | .02–.04 | .026 | .01 |
| AB103.1 [pYGAI7] | 8 | .38–1.0 | .62 | .24 | .03–.06 | .043 | .01 |
| AB103.1 [pYGAI8] | 8 | .03–.18 | .09 | .05 | .003–.02 | .007 | .003 |

[1]A minimum of three independent transformants were tested.
[2]Secreted cross-reactive insulin-like-material (ILM) was determined by a competition radioimmune assay with $^{125}$I-labeled insulin and insulin standards. Data is reported as ILM secreted per ml of culture and as ILM secreted per ml normalized to a culture cell density with an absorbance at wavelength 650 mμ of 1.

Example II

This example compares the expression of a full-length α-factor leader construct, retaining all glycosylation sites, to an expression construct employing a truncated α-factor sequence retaining only a single glycosylation site at $Asn_{23}$. The non-yeast protein employed in this example is a human proinsulin analog wherein the connecting "C" peptide has been replaced by a yeast KEX2 endopeptidase cleavage site.

A. pYGAIC3

The plasmid pGAIC3 was made by replacing the 231 bp HindIII-SalI fragment of pGAI1 which encodes amino acids 14 through 30 of the B chain, the C-peptide, the A chain and 2 translation stop codons with a 132 bp synthetic HindIII-SalI gene fragment (shown in FIG. 3) which encodes amino acids 14 through 30 of the B chain, a Lys-Arg KEX2 endopeptidase cleavage site, the A chain, and translation stop codons. The plasmid pYGAIC3 was prepared from pGAIC3 as follows.

Plasmid pGAIC3 was digested with BamHI, and the 1107 bp BamHI expression cassette containing the GAPDH promoter, the sequence encoding α-factor leader linked to proinsulin analog, and the α-factor transcription terminator was isolated and ligated into BamHI digested and phosphatase-treated pAB24, and then cloned in *E. coli.* Plasmid pYGAIC3 was obtained, in which the expression cassette was oriented such that the GAPDH promoter was proximal to the unique SalI site of the vector.

B. $pY\alpha f_L7C3$

Plasmid $pY\alpha F_L7C3$ contains DNA encoding the truncated α-factor leader described above for pYGAI7 linked to the sequence for the proinsulin analog, also described above (pYGAIC3). This plasmid was constructed as follows.

First, pGAIC3 was cut with HindIII and SalI, and a 132 bp fragment was gel isolated. This fragment contains sequences encoding all but the first 12 codons of the proinsulin analog. It was ligated into a gel isolated 4640 bp fragment from HindIII- and Sail-digested pGAI7 to provide plasmid $p\alpha f_L7C3$. After cloning in *E. coli,* this plasmid was cut with BamHI and a 1062 bp BamHI fragment was gel isolated. This expression cassette contains the truncated α-factor leader construct of pGAI7 with the proinsulin analog in place of the normal proinsulin sequence. The expression cassette was then ligated into the BamHI site of pAB24, as described above, to give $pY\alpha f_L7C3$.

Comparative Expression

Expression levels were determined for pYGAIC3 and $pY\alpha f_L7C3$ in two strains of *S. cerevisiae.* Strain AB103.1 has been described in Example I. Strain AB110-4 is a derivative of Saccharomyces cerevisiae strain AB110 (Matα, leu2, ura3-52, pep4-3, his4-580[cir°]) in which a deletion has been engineered into the pep4 gene. These strains were transformed as described above with plasmids pYGAIC3, and $pY\alpha f_L7C3$, and ura prototrophs were selected. Inoculum cultures were grown in SD-leu [Sherman et al., supra.] at 30° C. for 24–48 hours then pelleted by centrifugation, washed and diluted 20 fold into $ura^-$ medium (described above) and grown for 48–72 hours at 30° C. Cell-free conditioned culture medium was prepared by centrifugation for assay in a competition insulin radioimmune assay.

The results are shown in Table 3. As can be seen the truncated α-factor construct mediates increased secretion of immunoreactive proinsulin analog, compared to the natural α-factor leader sequence.

TABLE 3

Secretion of ILM from a Proinsulin Analog Construct Mediated by a Truncated α-Factor Leader or Natural α-Factor Leader

| | | ILM[2] | | | | | |
|---|---|---|---|---|---|---|---|
| | No. of | μg/ml | | | μg/ml $OD_{650}$ | | |
| Transformant | Tests[1] | Range | Mean | Std. dev. | Range | Mean | Std. dev. |
| AB103.1 [pYGA1C3] | 6 | 1–2.75 | 1.66 | .65 | .11–.20 | .14 | .04 |
| AB103.1 [pyαf$_L$7C3] | 6 | 1.5–6.63 | 4.46 | 2.15 | .14–.60 | .40 | .19 |
| AB110.4 [pYGAIC3] | 3 | 1.15–1.4 | 1.28 | .13 | .10–.12 | .11 | .01 |
| AB110.4 [pyαf$_L$7C3] | 3 | 2.15–4.12 | 3.46 | 1.14 | .19–.38 | .31 | 10 |

[1]A minimum of three independent transformants were tested.
[2]Secreted cross-reactive insulin-like-material (ILM) was determined by a competition radioimmune assay with $^{125}$I-labeled insulin and insulin standards. Results are reported as amounts of ILM per ml of culture and as amount secreted per ml normalized to a cell density with an absorbance at 650 mμ wavelength = 1.

Example III

This example describes the construction of a truncated α-factor expression vector which mediates increased levels of active insulin-like growth factor-1.

First, a DNA sequence encoding a truncated α-factor leader and a coding sequence for IFG1 was prepared. A synthetic sequence was prepared by standard procedures employing an Applied Biosystems 380A DNA synthesis machine according to manufacturer's direction. Fourteen DNA sequences were synthesized ranging from 22 to 57 bases in length, purified by PAGE, and phosphorylated individually by T4 kinase in the presence of ATP. The sequences were then annealed and ligated by standard procedures.

The sequence of the synthetic gene is shown in FIG. 5. The purified synthetic gene fragment was cloned into NcoI/SalI digested pBS100 (described below). The resulting plasmid was called pBS100 Tαf$_L$ IGF1.

Plasmid pBS100 contains a yeast expression cassette cloned into a pBR322 derivative, pAB12. The expression cassette contains the hybrid ADH-2/GAPDH promoter and the GAPDH terminator flanking a non-essential gene segment. The ADH-2/GADPH promoter is a 1200 bp BamHI-NcoI fragment isolated from pJS103 (see below) and the GAPDH terminator is a 900 bp SalI-BamHI fragment isolated from plasmid pPAG1. EPO Publication No. 164,556. Plasmid pBS100 also contains a non-essential fragment between NcoI and SalI sites which is replaced by gene fragments of interest. The expression cassette can be removed from pBS100 by digestion with BamHI and cloned into yeast shuttle vectors for introduction into yeast cells.

Plasmid pJS103, which contains the hybrid ADH-2/GAPDH promoter employed above, was constructed as follows. The ADH-2 portion of the promoter was constructed by cutting a plasmid containing the wild-type ADH2 gene from plasmid pADR2 [Beier et al. (1982) Nature 300:724–728] with restriction enzyme EcoR5, which cuts at position +66 relative to the ATG start codon, as well as in two other sites in pADR2, outside of the ADH2 region. The resulting mixture of a vector fragment and two smaller fragments was reacted with Ba131 exonuclease to remove about 300 bp. Synthetic XhoI linkers were ligated onto the Ba131-treated DNA. The resulting DNA linker vector fragment (about 5 kb) was separated from the linkers by column chromatography, cut with restriction enzyme XhoI, religated, and used to transform *E. coli* to ampicillin resistance. The positions of the XhoI linker were determined by DNA sequencing. One plasmid which contained an XhoI linker within the 5' nontranscribed region of the ADH2 gene (position −232 from ATG) was cut with the restriction enzyme XhoI, treated with nuclease S1, and subsequently treated with the restriction enzyme EcoRI to create a linear vector molecule having 1 blunt end at the site of the XhoI linker and an EcoRI end. The GAPDH portion of the promoter was constructed by cutting plasmid pPGAP [EPO Publication No. 164,556] with the enzymes BamHI and EcoRI, followed by the isolation of the 0.4 Kbp DNA fragment. This purified fragment was then completely digested with the enzyme AluI and an approximately 200 bp fragment was isolated. This GAPDH promoter fragment was ligated to the ADH-2 fragment present on the linear vector described above to give plasmid JS103.

Figure 6:
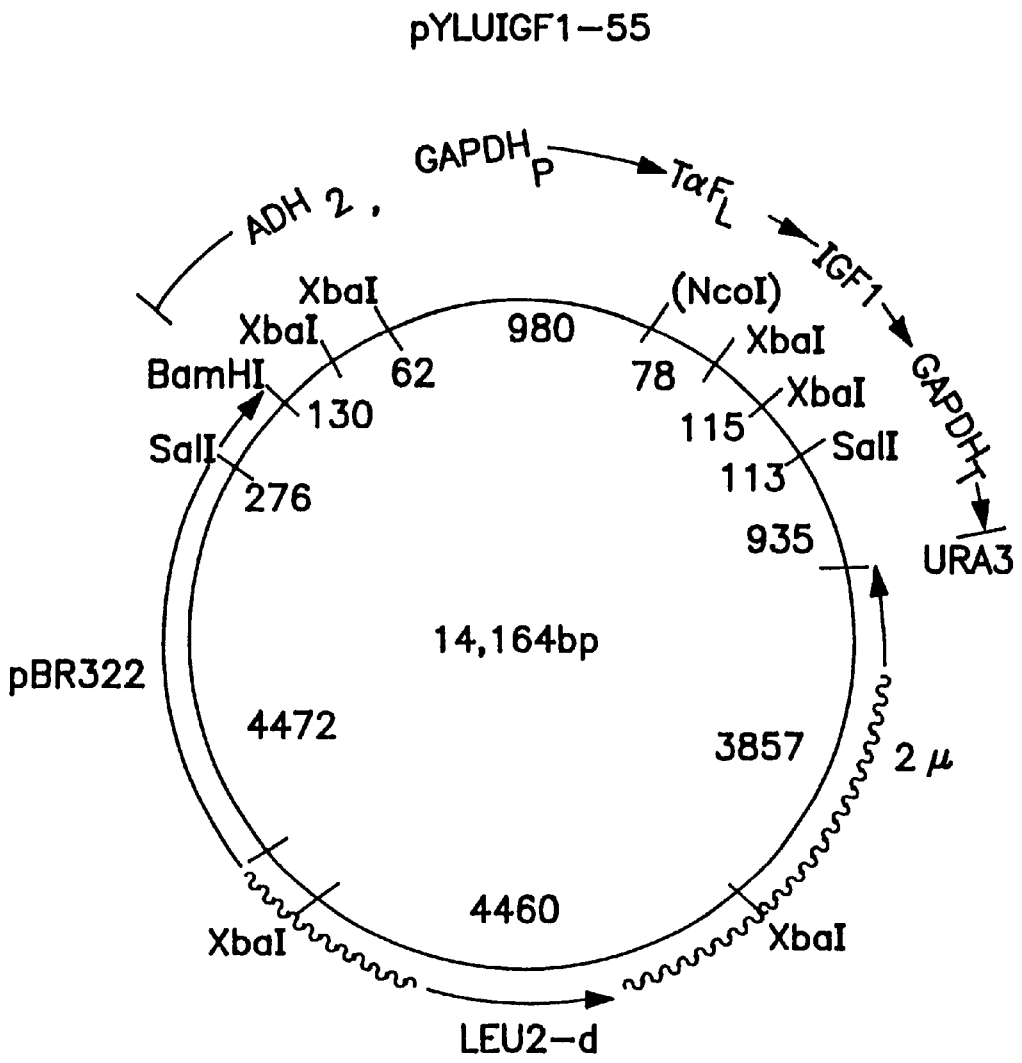
FIG. 6 is a restriction map of pYLUIGF1-55, an expression vector described in Example III encoding IGF1 under the control of a truncated α-factor leader.

A BamHI fragment was then isolated from pBS100 Tα$_{fL}$ IGF1. This fragment contains the ADH2/GAPDH promoter, a truncated α-factor leader (AA 1–25, 81–83) a LysArg processing site, a coding sequence for IGF1, and the GAPDH terminator sequence. This BamHI fragment was then cloned into pAB24, previously digested with BamHI. A positive clone was selected, and while initially called plasmid 18.5, it was subsequently named pYLUIGF1-55. (See FIG. 6.)

Figure 7:
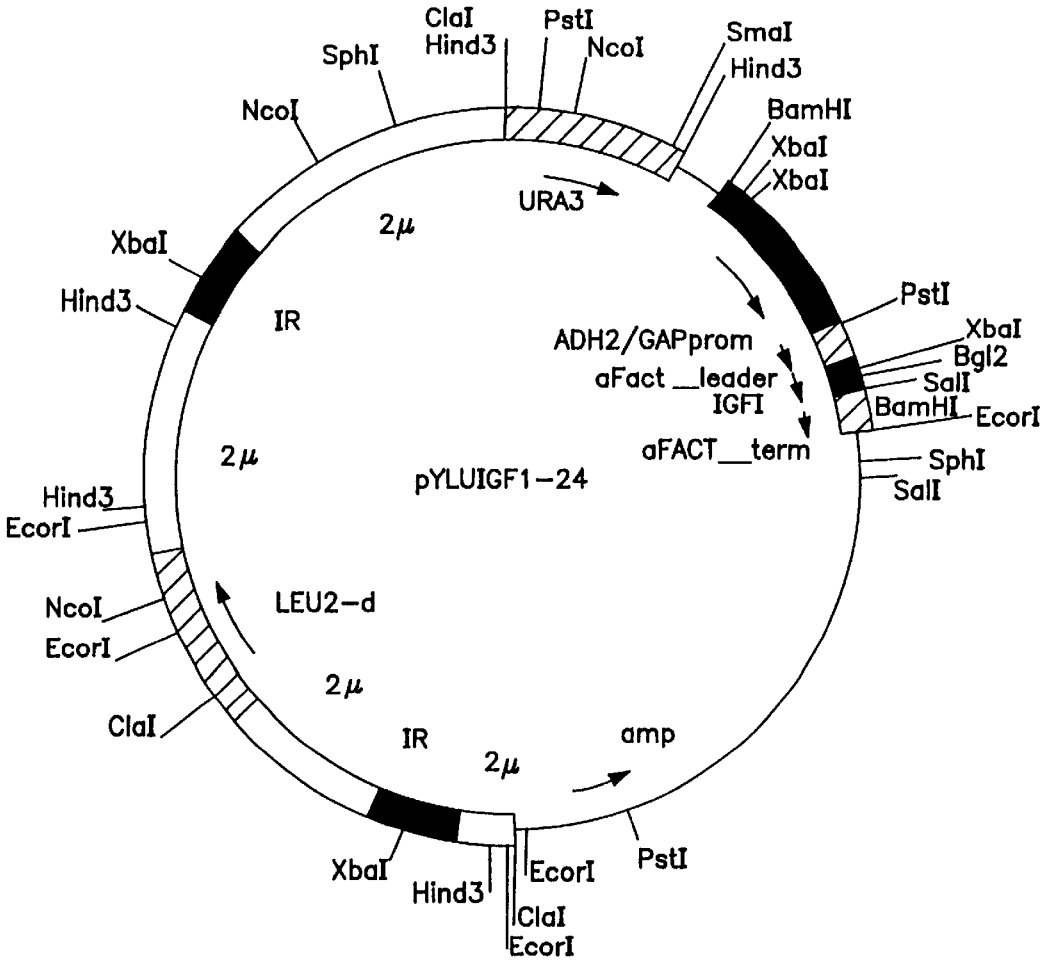
FIG. 7 is a restriction map of pYLUIGF1-24, an expression vector described in Example III encoding IGF1 under the control of a full-length α-factor leader with three glycosylation sites.

A second expression vector, pYLUIGF1-24 was also prepared by analogous methods. A restriction map is shown in FIG. 7. This vector is similar to pYLUIGF1-55, except that it has a full-length α-factor leader directing secretion with three glycosylation sites (compare Example I.A.) and the α-factor terminator.

Yeast strain AB110 (EPO Publication No. 164,556) was transformed with pYLUIGF1-55 and pYLUIGF1-24 by conventional spheroplasting techniques [Hinnen et al. (1978) Proc. Natl. Acad. Sci. USA 75:1919–1933], and expression compared.

The expression of IGF1 from AB110 (pYLUIGF1-55) and AB110 (pYLUIGF1-24) is non-constitutive. Induction of IGF1 expression was achieved by bringing about a low concentration of glucose in the growth medium. Under standard conditions, shake flask cultures (25 ml) fully utilize the glucose in the medium by 18–24 hours post inoculation. Thus, 25 ml cultures of AB110 (pYLUIGF1-55) and AB110 (pXLUIGF1-24) were grown under standard conditions for 72 hours. Supernatant samples were taken at 49 and 72 hours post inoculation and assayed for IGF1 biological activity (RigA) and for immunoreactivity (RIA) with anti-IGF1 antibodies. As can be seen, pYLUIGF1-55, with a truncated α-factor leader, secreted protein of which a substantially greater fraction was biologically active. Although pYLUIGF1-24 secreted more protein that showed reactivity with IGF1 antibodies, relatively little of this protein was biologically active.

The results are shown in Table 4. The radioreceptor assay (RRA) measures the ability of IGF-1 to bind to its receptor. This is a measure of the biological activity of recombinant polypeptide since it is believed that IGF-1 exerts all of its activity through its receptor. The receptor assay is described in Marshall et al. (1974) J. Clin. Endorinol. Metab. 19:283–292. The radioimmunoassay (RIA) is a competitive assay that measures the amount of protein antigenically cross-reactive with native IGF-1, whether or not it is biologically active. The assay is described in Zapf et al. (1981) J. Clin. Invest. 68:1321–1330.

TABLE 4

Secretion of IGF1 Mediated by a Truncated α-Factor Leader or a Natural α-Factor Leader

| Transformant | 49 hrs | | | |
|---|---|---|---|---|
| 72 hrs | RRA[1] | RIA[2] | RRA | RIA |
| AB110 (pYLUIGF1-55) | 1.0 | 14 | 1.3 | 14 |
| AB110 (pYLUIGF1-24) | 1.3 | 54 | 2.7 | 66 |

[1]μg/ml
[2]μg/ml

Deposit of Biological Materials

The following expression vectors were deposited with the American Type Culture Collection (ATCC), 12301 Parklawn Drive, Rockville, Md., U.S.A., and will be maintained under the provisions of the Budapest Treaty. The accession numbers and dates of deposit are listed below.

| Deposited Material | ATCC Number | Deposit Date |
|---|---|---|
| *E. coli* (pYGAI7) | 67597 | 12/29/87 |
| *E. coli* (pYα$f_1$7C3) | 67596 | 12/29/87 |
| *E. coli* (pYLUIGFI-55) | 67595 | 12/29/87 |

These deposits are provided for the convenience of those skilled in the art. These deposits are neither an admission that such deposits are required to practice the present invention nor that equivalent embodiments are not within the skill of the art in view of the present disclosure. The public availability of these deposits is not a grant of a license to make, use or sell the deposited materials under this or any other patent. The nucleic acid sequences of the deposited materials are incorporated in the present disclosure by reference, and are controlling if in conflict with any sequences described herein.

Although the foregoing invention has been described in some detail for the purpose of illustration, it will be obvious that changes and modifications may be practiced within the scope of the appended claims by those of ordinary skill in the art.

I claim:

1. A yeast cell comprising a DNA construct that provides for the expression and secretion of a non-yeast protein, said DNA construct comprising a yeast recognized transcription initiation sequence, linked 5' to a coding sequence under the control of both said yeast recognized transcription initiation sequence and a yeast-recognized termination sequence, said yeast-recognized termination sequence being 3' to said coding sequence, wherein said coding sequence encodes a precursor polypeptide comprised of a leader sequence and said non-yeast protein linked by a processing site that provides for the cleavage of said non-yeast protein from said precursor polypeptide, wherein said leader sequence is about the first 25 to about the first 50 N-terminal residues of a yeast alpha-factor leader polypeptide, comprises a single yeast alpha-factor precursor glycosylation site and comprises a single peptide of a yeast alpha-factor precursor comprising the first about 19 to about 23 N-terminal residues of said alpha-factor precursor.

2. The cell of claim 1 wherein said non-yeast protein is a mammalian protein.

3. The cell of claim 2 wherein said mammalian protein is a precursor of human insulin.

4. The cell of claim 3 wherein said precursor of human insulin is human proinsulin.

5. The cell of claim [3] *1* wherein said [precursor of human insulin] *non-yeast protein* comprises insulin a chain and insulin b chain linked by a yeast-recognized processing site cleaved in vivo.

6. The cell of claim 5 wherein said processing site is cleaved by the KEX2 gene product of Saccharomyces.

7. The cell of claim 2 wherein said mammalian protein is insulin-like growth factor I.

8. The cell of claim 1 wherein said yeast cell is from the genus Saccharomyces.

9. The cell of claim 8 wherein said yeast cell is *S. cerevisiae.*

10. The cell of claim 8 wherein yeast α-factor precursor is *S. cerevisiae* MFα1.

11. The cell of claim 1 wherein said leader sequence is about 28 to about 40 N-terminal residues of said precursor polypeptide.

12. The cell of claim 1 wherein said leader sequence is about 35 contiguous N-terminal residues of a yeast alpha-factor precursor polypeptide.

13. A double-stranded DNA molecule comprising a region encoding a precursor polypeptide secretable by a yeast host, said region, with reference to one of the strands, [having] *comprising* the structure:

5'-AF-CHO-$X_n$-S-Gene*-3' wherein

AF encodes a yeast alpha-factor signal peptide;

CHO encodes a [yeast alpha-factor precursor] glycosylation site *comprising the amino acid sequence Asn-Y-Y' wherein Y is any amino acid and Y' is Thr or Ser;*

$X_n$ encodes a spacer polypeptide of n amino acids in length that does not contain a glycosylation site or a processing site that provides for cleavage of said precursor polypeptide in vivo by yeast;

n is an integer from 0 to 30;

Gene* encodes a non-yeast protein; and

S encodes a processing site that provides for cleavage of said precursor polypeptide.

14. The DNA molecule of claim 13 wherein AF encodes a polypeptide of about 19 to 23 amino acids in length.

15. The DNA molecule of claim 13 wherein n is an integer from about 0 to about 20.

16. The DNA molecule of claim 13 wherein n is an integer from about 0 to about 10.

17. The DNA molecule of claim 13 wherein n is an integer from about 3 to about 10.

18. The DNA molecule of claim 13 wherein said yeast host is a Saccharomyces.

19. The DNA molecule of claim 13 wherein said yeast α-factor signal peptide is a Saccharomyces signal peptide.

20. The DNA molecule of claim 13 wherein S encodes a processing site recognized in vivo by said yeast host.

21. The DNA molecule of claim 20 wherein S encodes a dipeptide recognized by the KEX2 endopeptidase.

22. The DNA molecule of claim 21 wherein said dipeptide is 5'-Lys-Arg-3' or 5'-Arg-Arg-3'.

23. The DNA molecule of claim 13 comprising a replicon.

24. The DNA molecule of claim 23 wherein said region encoding said precursor polypeptide is under the control of yeast-recognized transcription initiation and termination sequences, and said replicon is a yeast replicon.

25. The DNA molecule of claim 24 wherein said replicon is a plasmid.

26. The DNA molecule of claim 24 wherein said replicon is a chromosome.

27. A DNA molecule comprising a nucleotide sequence that encodes about the first 25 to about the first 50 contiguous N-terminal amino acids of a yeast alpha-factor precursor leader sequence that includes a single yeast alpha-factor precursor leader sequence glycosylation site and no other yeast alpha-factor precursor leader sequence glycosylation site.

28. The DNA molecule of claim 27 wherein the nucleotide sequence encodes about the first 25 to about the first 40 contiguous N-terminal amino acids of a yeast alpha-factor precursor leader sequence that includes a single yeast alpha-factor precursor leader sequence glycosylation site and no other yeast alpha-factor precursor leader sequence glycosylation site.

29. The DNA molecule of claim 27 wherein the nucleotide sequence encodes about the first 35 contiguous N-terminal amino acids of a yeast alpha-factor precursor leader sequence that includes a single yeast alpha-factor precursor leader sequence glycosylation site and not other yeast alpha-factor precursor leader sequence glycosylation site.

30. The DNA molecule of claim 27 wherein the nucleotide sequence encodes about the first 28 contiguous N-terminal amino acids of a yeast alpha-factor precursor leader sequence that includes a single yeast alpha-factor precursor leader sequence glycosylation site and no other yeast alpha-factor precursor leader sequence glycosylation site.

31. The DNA molecule of claim 27 wherein the nucleotide sequence encodes amino acids 1–25 and 81–83 of a yeast alpha-factor precursor leader sequence.

*32. A method for producing a recombinant protein, said method comprising:*

*providing a yeast cell as defined in claim 1, and*

*culturing said yeast cell under conditions that provide for expression and secretion of said non-yeast protein.*

*33. The method of claim 32 wherein said non-yeast protein is a mammalian protein.*

*34. The method of claim 32 wherein said non-yeast protein is a precursor of human insulin.*

*35. The method of claim 34 wherein said precursor of human insulin is human proinsulin.*

*36. The method of claim 34 wherein said precursor of human insulin comprises insulin a chain and insulin b chain linked by a yeast-recognized processing site cleaved in vivo.*

*37. The method of claim 36 wherein said processing site is cleaved by the KEX2 gene product of Saccharomyces.*

*38. The method of claim 33 wherein said mammalian protein is insulin-like growth factor I.*

*39. The method of claim 32 wherein said yeast cell is from the genus Saccharomyces.*

*40. The method of claim 39 wherein said yeast cell is S. cerevisiae.*

*41. The method of claim 39 wherein said yeast alpha-factor leader polypeptide is from S. cerevisiae MFα1.*

*42. The method of claim 32 wherein said leader sequence is about the first 28 to about the first 40 N-terminal amino acid residues of a yeast alpha-factor leader polypeptide.*

*43. The method of claim 32 wherein said leader sequence is about the first 35 contiguous N-terminal residues of a yeast alpha-factor leader polypeptide.*

*44. A method of producing a recombinant protein, said method comprising:*

*transforming a yeast cell with a DNA construct that provides for the expression and secretion of a non-yeast protein, wherein said DNA construct comprises the double-stranded DNA molecule as defined in claim 13, and*

*culturing said transformed yeast cell under conditions that provide for expression and secretion of said non-yeast protein.*

*45. The method of claim 44 wherein AF encodes a polypeptide of about 19 to 23 amino acids in length.*

*46. The method of claim 44 wherein n is an integer from about 0 to about 20.*

*47. The method of claim 44 wherein n is an integer from about 0 to about 10.*

*48. The method of claim 44 wherein n is an integer from about 3 to about 10.*

*49. The method of claim 44 wherein said yeast host is a Saccharomyces.*

*50. The method of claim 44 wherein said yeast alpha-factor signal peptide is a Saccharomyces signal peptide.*

*51. The method of claim 44 wherein S encodes a processing site recognized in vivo by said yeast host.*

*52. The method of claim 51 wherein S encodes a dipeptide recognized by the KEX2 endopeptidase.*

*53. The method of claim 52 wherein said dipeptide is 5'-Lys-Arg-3' or 5'-Arg-Arg-3'.*

*54. The method of claim 44 wherein said DNA molecule comprises a replicon.*

*55. The method of claim 54 wherein said region encoding said precursor polypeptide is under the control of yeast-recognized transcription initiation and termination sequences, and said replicon is a yeast replicon.*

*56. The method of claim 55 wherein said replicon is a plasmid.*

*57. The method of claim 55 wherein said replicon is a chromosome.*

*58. A method of producing a recombinant protein, said method comprising:*

*transforming a yeast cell with a DNA construct that provides for the expression and secretion of a non-yeast protein, wherein said DNA construct comprises the double-stranded DNA molecule as defined in claim 27, and*

*culturing said transformed yeast cell under conditions that provide for expression and secretion of said non-yeast protein.*

*59. The method of claim 58 wherein the nucleotide sequence encodes about the first 25 to about the first 40 contiguous N-terminal amino acids of a yeast alpha-factor precursor leader sequence that includes a single yeast alpha-factor precursor leader sequence glycosylation site and no other yeast alpha-factor precursor leader sequence glycosylation site.*

*60. The method of claim 58 wherein the nucleotide sequence encodes about the first 35 contiguous N-terminal amino acids of a yeast alpha-factor precursor leader sequence that includes a single yeast alpha-factor precursor leader sequence glycosylation site and no other yeast alpha-factor precursor leader sequence glycosylation site.*

*61. The method of claim 58 wherein the nucleotide sequence encodes about the first 28 contiguous N-terminal amino acids of a yeast alpha-factor precursor leader sequence that includes a single yeast alpha-factor precursor leader sequence glycosylation site and no other yeast alpha-factor precursor leader sequence glycosylation site.*

*62. The method of claim 59 wherein the nucleotide sequence encodes amino acids 1–25 linked to amino acids 81–83 of a yeast alpha-factor precursor leader sequence.*

*63. The method of claim 44 wherein CHO encodes a yeast alpha-factor precursor glycosylation site.*

*64. The DNA molecule of claim 13 wherein CHO encodes a yeast alpha-factor precursor glycosylation site.*

*65. The method of claim 49 wherein said yeast host is S. cerevisiae.*

*66. The method of claim 49 wherein the leader construct AF-CHO-$X_n$-S is about the first 25 to about the first 40 contiguous N-terminal residues of a yeast alpha-factor signal peptide.*

*67. The method of claim 49 wherein the leader construct AF-CHO-$X_n$-S is about the first 28 to about the first 40 contiguous N-terminal residues of a yeast alpha-factor signal peptide.*

*68. The method of claim 49 wherein the leader construct AF-CHO-$X_n$-S is about the first 35 to about the first 40 contiguous N-terminal residues of yeast alpha-factor signal peptide.*

*69. The method of claim 68 wherein said non-yeast protein is a human proinsulin.*

*70. The method of claim 69 wherein said DNA construct is plasmid pYGAI7 (ATCC Accession Number 67597).*

*71. The method of claim 69 wherein said human proinsulin comprises insulin a chain and insulin b chain linked by a yeast-recognized processing site cleaved in vivo by the KEX2 gene product of Saccharomyces.*

*72. The method of claim 71 wherein said DNA construct is plasmid pY$\alpha f_L$7C3 (ATCC Accession Number 67596).*

*73. The method of claim 49 wherein the leader construct AF-CHO-$X_n$-S is amino acids 1–25 linked to amino acids 81–83 of a yeast alpha-factor signal peptide.*

*74. The method of claim 73 wherein said non-yeast protein is insulin-like growth factor I.*

*75. The method of claim 74 wherein said DNA construct is plasmid pYLUIGFI-55 (ATCC Accession Number 67595).*

* * * * *